US010420727B2

(12) United States Patent
Malhotra et al.

(10) Patent No.: US 10,420,727 B2
(45) Date of Patent: *Sep. 24, 2019

(54) PHARMACEUTICAL ANTIRETROVIRAL COMPOSITION

(71) Applicant: Cipla Limited, Mumbai (IN)

(72) Inventors: Geena Malhotra, Mumbai (IN); Shrinivas Purandare, Mumbai (IN)

(73) Assignee: Cipla Limited, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/972,655

(22) Filed: May 7, 2018

(65) Prior Publication Data

US 2018/0250271 A1 Sep. 6, 2018

Related U.S. Application Data

(63) Continuation of application No. 14/429,651, filed as application No. PCT/GB2013/000453 on Oct. 23, 2013, now Pat. No. 10,004,721.

(30) Foreign Application Priority Data

Oct. 23, 2012 (IN) .................. 3093/MUM/2012

(51) Int. Cl.
*A61K 9/20* (2006.01)
*A61K 9/22* (2006.01)
*A61K 9/26* (2006.01)
*A61K 9/24* (2006.01)
*A61K 47/00* (2006.01)
*A61K 31/535* (2006.01)
*A61K 31/505* (2006.01)
*A61K 31/415* (2006.01)
*A61K 31/473* (2006.01)
*A61K 31/513* (2006.01)
*A61K 31/52* (2006.01)
*A61K 31/5365* (2006.01)
*A61K 9/28* (2006.01)
*A61K 9/50* (2006.01)
*A61K 31/4178* (2006.01)
*A61K 31/536* (2006.01)
*A61K 45/06* (2006.01)
*A61K 9/48* (2006.01)
*A61K 31/675* (2006.01)

(52) U.S. Cl.
CPC .............. *A61K 9/209* (2013.01); *A61K 9/20* (2013.01); *A61K 9/2009* (2013.01); *A61K 9/2013* (2013.01); *A61K 9/2054* (2013.01); *A61K 9/2095* (2013.01); *A61K 9/28* (2013.01); *A61K 9/2866* (2013.01); *A61K 9/4833* (2013.01); *A61K 9/5084* (2013.01); *A61K 31/4178* (2013.01); *A61K 31/473* (2013.01); *A61K 31/513* (2013.01); *A61K 31/52* (2013.01); *A61K 31/536* (2013.01); *A61K 31/5365* (2013.01); *A61K 31/675* (2013.01); *A61K 45/06* (2013.01); *A61K 2300/00* (2013.01)

(58) Field of Classification Search
None
See application file for complete search history.

(56) References Cited

U.S. PATENT DOCUMENTS

| 7,432,294 B2 | 10/2008 | Alani et al. |
| 10,004,721 B2 | 6/2018 | Malhotra et al. |
| 2009/0324729 A1 | 12/2009 | Koziara et al. |
| 2010/0183716 A1 | 7/2010 | Koo et al. |
| 2012/0213851 A1 | 8/2012 | Mahjour et al. |
| 2012/0244212 A1 | 9/2012 | Guilford |

FOREIGN PATENT DOCUMENTS

| CN | 102655752 A | 9/2012 |
| EP | 1083932 A1 | 3/2001 |
| IN | 3093MUM2012 | 10/2012 |
| WO | 9955372 A1 | 11/1999 |
| WO | 2004087169 A1 | 10/2004 |
| WO | 2008043829 A2 | 4/2008 |
| WO | 2008103949 A1 | 8/2008 |
| WO | 2009135179 A2 | 11/2009 |
| WO | 2011053504 A1 | 5/2011 |
| WO | 2011094150 A1 | 8/2011 |
| WO | 2011127244 A2 | 10/2011 |
| WO | 2012151165 A1 | 11/2012 |
| WO | 2014064409 A1 | 5/2014 |

OTHER PUBLICATIONS

Foreign communication from a related application—First Office Action of Mexican Patent Application No. MX/a/2015/003730, dated Dec. 7, 2017, with English summary, 7 pages.
Foreign communication from a related application—Second Office Action of Mexican Patent Application No. MX/a/2015/003730, dated Jul. 13, 2018, with English summary, 8 pages.
Foreign communication from a related application—Examination Report of Indian Application No. 655/MUMNP/2015, dated Sep. 7, 2018, 6 pages.
Ananworanich, Jintanat, et al., "Failures of 1 week on, 1 week off antiretroviral therapies in a randomized trial," AIDS, 2003, pp. F33-F37, vol. 17, No. 15, Lippincott Williams & Wilkins.
Chen, Huabing, et al., "Nanonization strategies for poorly water-soluble drugs," Drug Discovery Today, Uncorrected Proof, Mar. 2010, pp. 1-7, Elsevier Ltd.

(Continued)

Primary Examiner — Jeffrey T. Palenik
(74) Attorney, Agent, or Firm — Conley Rose, P.C.; Rodney B. Carroll

(57) ABSTRACT

A pharmaceutical composition comprises at least one integrase inhibitor or its salt, solvate, complex, hydrate, isomer, ester, tautomer, anhydrate, enantiomer, polymorph or prodrug and at least one antiretroviral or anti-HIV agent or its salt, solvate, complex, hydrate, isomer, ester, tautomer, anhydrate, enantiomer, polymorph or prodrug.

11 Claims, No Drawings

(56) References Cited

OTHER PUBLICATIONS

Foreign communication from the priority application—International Search Report and Written Opinion, PCT/GB2013/000453, dated Nov. 29, 2013, 11 pages.

Prejean, Joseph, et al., "Estimated HIV Incidence in the United States, 2006-2009," www.plosone.org, Aug. 2011, pp. 1-13, vol. 6, No. 8, e17502, PLoS ONE.

Schrijvers, Rik, et al., "Combinational therapies for HIV: a focus on EVG/COBI/FTC/TDF," Drug Evaluation, 2012, pp. 1969-1983, vol. 13, No. 13, Informa UK, Ltd.

Coffey, Susa, "Dolutegravir in Initial Therapy: Two Phase 2 Studies," HIV InSite, published Oct. 5, 2012, http://hivinsite.ucsf.edu/insite?page=hmq-1210-01, 2 pages.

Highleyman, Liz, "Dolutegravir matches raltegravir for people starting treatment," HIV & AIDS Information, published Jul. 27, 2012, http://www.aidsmap.com/print/Dolutegravir-matches-raltegravir-for-people-starting-treatment/page/2454936, 2 pages.

Foreign Communication from a related counterpart application—First Office Action of Chinese Application No. 201380050135.2 dated Jul. 15, 2016, with English translation, 11 pages.

Foreign Communication from a related counterpart application—Examination Report No. 1 of Australian Patent Application No. 2013336491 dated Jul. 17, 2017, 4 pages.

Foreign Communication from a related counterpart application—First Examination Report of New Zealand Patent Application No. 706223 dated Nov. 27, 2017, 3 pages.

Foreign Communication from a related counterpart application—Further Examination Report of New Zealand Patent Application No. 706223 dated Jun. 5, 2018, 4 pages.

PHARMACEUTICAL ANTIRETROVIRAL COMPOSITION

CROSS REFERENCE TO RELATED APPLICATIONS

This application is a continuation of and claims priority to U.S. patent application Ser. No. 14/429,651 filed Mar. 19, 2015, published as U.S. Patent Publication US 2015-01231079 A1, which is a filing under 35 U.S.C. 371 of International Application No. PCT/GB2013/000453 filed Oct. 23, 2013, entitled "Pharmaceutical Antiretroviral Composition," which claims priority to Indian Patent Application No. 3093/MUM/2012 filed Oct. 23, 2012, which applications are incorporated by reference herein in their entirety.

FIELD OF THE INVENTION

The present invention relates to a pharmaceutical composition comprising anti-retroviral agents, the manufacturing process thereof and use of the said composition for the prevention, treatment or prophylaxis of retroviral diseases in the patients in need thereof.

BACKGROUND AND PRIOR ART

The human immunodeficiency virus ("HIV") is the causative agent for acquired immunodeficiency syndrome ("AIDS"), a disease characterized by the destruction of the immune system, particularly of CD4 T-cells with susceptibility to opportunistic infections. In nearly all cases where individuals receive no treatment for HIV infection, the proliferation of the virus gives rise to AIDS. As of early 1999, an estimated 33.4 million people are infected with HIV worldwide. Furthermore, in 2009 approximately 50,000 people were newly infected with HIV in the United States [Prejean J, Song R, Hernandez A, et al. *Estimated HIV incidence in the United States,* 2006-2009. PLoS ONE 2011; 6(8): e7502]. It has also been observed that the annual rate of new infection with HIV in the entire human population has not declined. Despite this fact, the rate of death due to AIDS has begun to drop in some nations primarily through the recent use of combination drug therapies against HIV infection.

The means by which such therapies counter HIV infection is best understood with reference to the biological mechanisms of the HIV life cycle. HIV is a member of a class of infectious agents known as retroviruses. The infectious form of HIV, a virion, is a particle that consists of a viral genome composed of RNA that is surrounded by proteins encoded by the genome. Infection occurs when an HIV virion enters a susceptible host cell, such as a T lymphocyte within the bloodstream. At this point, one of the viral proteins that comprise the virion, reverse transcriptase (RT), synthesizes a double-stranded DNA copy of the HIV RNA genome. The resulting HIV DNA enters the cell nucleus as part of a stable complex with other virion proteins. This complex contains all the necessary molecular apparatus for integration wherein the HIV DNA is covalently inserted into the host cell's genomic DNA which is absolutely required for prolific HIV infection. It is only after integration that the HIV DNA can serve as the template for the production of HIV proteins and RNA that will comprise progeny virions. Among these viral proteins is the HIV protease, the activity of which is necessary for proper formation of new virions. This process, from viral entry to new virion production, is termed viral replication. Upon release from an infected host cell, the newly produced virions are capable of further infecting uninfected host cells. It is through successive rounds of HIV replication and productive host cell infection that HIV disease spreads throughout numerous host cells and ultimately progresses to AIDS.

The current strategy recommended for the treatment of HIV infection is Highly Active Antiretroviral Therapy (HAART). HAART normally consists of a combination of antiretroviral drugs (ARV) taken together. These therapies consist of simultaneous or separate administration of combination of drugs, which potently and selectively target different elements of the HIV life cycle to disrupt or forestall productive HIV infection and progression to AIDS.

For example WO2008043829 discloses a method of treating HIV wherein emtricitabine, tenofovir and nevirapine are administered once a day.

WO04087169 discloses a composition useful for the treatment or prophylaxis of viral infections comprising nevirapine and at least one antiviral active compound such as alovudine.

US20100183716 discloses compressed tablets containing atazanavir sulfate, optionally with another active agents, e.g., anti-HIV agents, granules that contain atazanavir sulfate and an intragranular lubricant that can be used to make the tablets, compositions comprising a plurality of the granules, processes for making the granules and tablets, and methods of treating HIV.

WO2011127244 discloses compressed tablets containing atazanavir sulfate and an acidifying agent, optionally with another active agent, e.g., anti-HIV agents.

U.S. Pat. No. 7,432,294 disclose composition comprising one or more solubilized HIV protease inhibiting compounds with other HIV protease inhibiting compound.

EP1083932 discloses homogeneous combination of abacavir, lamivudine, and zidovudine in an amount which achieves antiviral efficacy.

Although the use of combination drug therapies against HIV has proven to be effective in many patients, the current drug regimens are far from ideal. Treatment failure often (though not always) occurs because a patient's strain of HIV may develop resistance to one or more of antiretroviral medications. The manner by which HIV develops resistance to antiretroviral drugs is similar to the way in which bacteria or mycobacterium develops resistance to antibiotics: for example election of insufficiently potent drug therapy for mutant strains that are resistant to the medications administered to the patient. These mutant strains then replace the wild-type strain due to their selective replication advantage in the face of drug pressure, leading to treatment failure.

Further the success of HAART depends on patient related factors as well, the most important being adherence. The HIV therapy is a life-long therapy coupled with high levels of adherence to the same. This is rather a demanding task for HIV infected patients due to various reasons such as low morale, social stigma, low immunity attributed to the disease. Some studies have also shown that adherence to prescribed drugs over long treatment periods is generally poor. (Jintanat A. et al. Swiss HIV Cohort Study. Failures of 1 week on, 1 week off antiretroviral therapies in a randomized trial AIDS, 2003; 17:F33-F37).

Hence, such non-adherence may lead to rebound in viral replication and, in presence of sub-optimal drug concentration may lead to rapid development of drug resistance. This development of drug resistance may be disastrous because of the complexity and cost associated with second line regimens and the potential for transmission of drug resistant virus in the community.

The therapy may involve use of different drug combinations, which are difficult to adhere, because of the different dosage forms for administering each such antiretroviral drug separately. This is of particular importance in the case of elderly patients.

Further for most of the therapeutic agents to produce systemic effects, the oral route still represents the preferred way of administration, owing to its several advantages and high patient compliance as compared to any other route of administration. Tablets and hard gelatin capsules still constitute a major portion of drug delivery systems that are currently available.

However, many patient groups such as the elderly, children, and patients who are mentally retarded, uncooperative, nauseated, or on reduced liquid-intake/diets have difficulties swallowing the dosage forms such as tablets and hard gelatin capsules. Further, those who are traveling or have little access to water are similarly affected.

Also, the route of drug administration, appearance, color, taste, tablet size and dosing regimen are most important parameters that govern patient compliance.

Especially, the geriatric and paediatric patients experience difficulty in swallowing larger sized tablets wherein large size tablet may result in esophageal damage due to its physical characteristics if it is not swallowed properly, which ultimately leads to poor patient compliance.

Also, oral administration of bitter drugs with an acceptable degree of palatability is a key issue for health care providers, especially for paediatric patients.

Further, there has been an enhanced demand for dosage forms that are more patient-friendly and patient compliant. Since the development cost of a new drug molecule is very high, efforts are now being made to focus on the development of new drug dosage forms for existing drugs with improved safety and efficacy together with reduced dosing frequency as well as which are cost-effective.

Although different treatment methods and dosage regimens have been framed in order to increase the patient adherence for treatment of HIV, there still remains a critical need for developing improved dosage forms such as a kit composition or dosage form by which a patient is encouraged to adhere to his daily dosage regimen. The combination of antiretroviral drugs administered in a single unit dosage form may result in increased patient compliance as the pill burden is reduced and dosing schedules are simplified. However, not all compounds are suitable for administration in combinations as there are several factors that influence the feasibility of combinations such as the chemical instability of the compounds, size of the dosage unit, potential for antagonistic or merely additive activities of the combined compounds, and difficulties in achieving a suitable formulation.

Thus there is an unmet need to find therapeutic agents suitable for use in combination to provide suitable pharmaceutical compositions to treat HIV infection and simultaneously increase the patient compliance.

OBJECT OF THE INVENTION

The object of the present invention is to provide a pharmaceutical composition which is a combination therapy to treat retroviral diseases, such as HIV.

Another object of the present invention is to provide a suitable pharmaceutical antiretroviral composition which would not only be convenient for patient administration but would also maintain patient adherence to the therapy.

Yet another object of the present invention is to provide a process of manufacturing such a pharmaceutical composition.

Another object of the present invention is to provide a method of prevention, treatment or prophylaxis of diseases caused by retroviruses, especially acquired immune deficiency syndrome or an HIV infection.

Yet another object of the present invention is to provide use of the pharmaceutical composition for the treatment or prophylaxis of diseases caused by retroviruses, especially acquired immune deficiency syndrome or an HIV infection.

SUMMARY OF THE INVENTION

According to one aspect of the present invention there is provided a pharmaceutical composition comprising at least one integrase inhibitor and at least one antiretroviral or anti-HIV agent and optionally one or more pharmaceutically acceptable excipients.

According to another aspect of the present invention there is provided a process for preparing the pharmaceutical composition wherein the process comprises admixing the at least one integrase inhibitor, the at least one antiretroviral or anti-HIV agent and optionally one or more pharmaceutically acceptable excipients.

According to a further aspect of the present invention, there is provided the pharmaceutical composition for use in medicine.

According to a further aspect of the present invention, there is provided the pharmaceutical composition for use in the prevention, treatment or prophylaxis of diseases caused by retroviruses, preferably acquired immune deficiency syndrome or an HIV infection.

According to another aspect of the present invention, there is provided the use of the pharmaceutical composition in the manufacture of a medicament for the prevention, treatment or prophylaxis of diseases caused by retroviruses, preferably acquired immune deficiency syndrome or an HIV infection.

According to another aspect of the present invention, there is provided a method of preventing or treating diseases caused by retroviruses, preferably acquired immune deficiency syndrome or an HIV infection, wherein the method comprises administering the pharmaceutical composition of the present invention to a subject in need thereof.

DETAILED DESCRIPTION

As discussed above, there is a need to develop and formulate a suitable pharmaceutical composition which would not only be convenient for patient administration but would also maintain patient adherence to the therapy. The inventors of the present invention have now surprisingly found combinations of integrase inhibitors with antiretroviral agents or anti-HIV agents for the treatment, prevention and prophylaxis of retroviral diseases.

The present invention thus provides a pharmaceutical composition comprising at least one integrase inhibitor and at least one anti-HIV or anti-retroviral agent optionally with pharmaceutically acceptable excipients.

Integrase inhibitors are a class of antiretroviral drug designed to block the action of integrase, a viral enzyme that inserts the viral genome into the DNA of the host cell. Since integration is a vital step in retroviral replication, blocking it can halt further spread of the virus.

The present invention thus provides a pharmaceutical composition comprising at least one integrase inhibitor and at least one antiretroviral agent or anti-HIV agent, optionally with at least one pharmaceutically acceptable excipients.

It will be appreciated that the respective therapeutic agents may be administered simultaneously or separately either in the same or different pharmaceutical compositions. If there is separate administration, it will also be appreciated that the subsequently administered therapeutic agents should be administered to a patient within a time scale so as to achieve, or more particularly optimize, synergistic therapeutic effect of such a combined preparation.

The term "pharmaceutical composition" includes tablets, capsules (filled with powders, pellets, beads, mini-tablets, pills, micro-pellets, small tablet units, MUPS, disintegrating tablets, dispersible tablets, granules, and microspheres, multiparticulates), sachets (filled with powders, pellets, beads, mini-tablets, pills, micro-pellets, small tablet units, MUPS, disintegrating tablets, dispersible tablets, granules, and microspheres, multiparticulates) and sprinkles, however, other dosage forms such as controlled release formulations, lyophilized formulations, modified release formulations, delayed release formulations, extended release formulations, pulsatile release formulations, dual release formulations and the like; liquid dosage form (liquids, suspensions, solutions, emulsions, microemulsions, sprays, spot-on), injection preparations, nano formulation etc. may also be envisaged under the ambit of the invention. Suitable excipients may be used for formulating the various dosage forms according to the present invention.

The term "integrase inhibitor(s)" (for example dolutegravir, elvitegravir or raltegravir) or "anti-HIV agent(s)" and "antiretroviral agent(s)" (for example nucleoside and nucleotide reverse transcription inhibitors (NRTIs), non-nucleoside reverse transcriptase inhibitors (NNRTIs), protease inhibitors (PIs), and maturation inhibitors (MIs)) used throughout the description and claims are used in a broad sense to include not only the active ingredient per se but also pharmaceutically acceptable derivatives thereof. Suitable derivatives include pharmaceutically acceptable salts, pharmaceutically acceptable solvates, pharmaceutically acceptable hydrates, pharmaceutically acceptable isomers, pharmaceutically acceptable esters, pharmaceutically acceptable anhydrates, pharmaceutically acceptable enantiomers, pharmaceutically acceptable polymorphs, pharmaceutically acceptable prodrugs, pharmaceutically acceptable tautomers and/or pharmaceutically acceptable complexes thereof and combinations thereof.

Examples of suitable integrase inhibitors include but are not limited to dolutegravir, raltegravir, MK-2048, JTK-656, elvitegravir.

Preferably, the integrase inhibitor is dolutegravir, raltegravir or elvitegravir.

The dose of dolutegravir is in the range of 1 to 50 mg, preferably in the range of 25 to 50 mg.

The dose of raltegravir is in the range of 25 to 500 mg. For example, 25, 100, 400, 500 mg. The preferred form of raltegravir is raltegravir potassium.

The dose of elvitegravir is in the range of 1 to 200 mg, preferably in the range of 25 to 180 mg.

Antiretroviral drugs/agents or the anti-HIV agents for the purpose of the present invention may be selected from nucleoside and nucleotide reverse transcription inhibitors (NRTIs), non-nucleoside reverse transcriptase inhibitors (NNRTIs), protease inhibitors (PIs), and maturation inhibitors (MIs) and any combination thereof.

The term "nucleoside and nucleotide reverse transcriptase inhibitors" (NRTIs) as used herein means nucleosides and nucleotides and analogues thereof that inhibit the activity of HIV-1 reverse transcriptase, the enzyme which catalyzes the conversion of viral genomic HIV-1 RNA into proviral HIV-1 DNA.

Suitable nucleoside reverse transcriptase inhibitors (NRTIs) that may be employed in the pharmaceutical composition of the present invention may comprise zidovudine; didanosine; stavudine; lamivudine; abacavir; adefovir; lobucavir; entecavir; apricitabine; emtricitabine; zalcitabine; dexelvucitabine; alovudine; amdoxovir; elvucitabine; AVX754; BCH-189; phosphazid; racivir; SP1093V; stampidine; BCH-10652, β-L-FD4 (also called β-L-D4C and named β-L-2',3'-dicleoxy-5-fluoro-cytidene); DAPD, the purine nucleoside, (−)-β-D-2,6-diamino-purine dioxolane; and lodenosine (FddA), 9(2,3-dideoxy-2-fluoro-β-D-threopentofuranosyl)adenine and any combination thereof.

Suitable nucleotide reverse transcriptase inhibitors (NtRTIs) that may be employed in the pharmaceutical composition of the present invention may comprise tenofovir and adefovir.

Preferably, the NRTIs/NtRTIs are selected from tenofovir, emtricitabine, lamivudine or zidovudine, or any combination thereof.

Suitable non-nucleotide reverse transcriptase inhibitors (NNRTIs) that may be employed in the pharmaceutical composition of the present invention may comprise nevirapine, rilpivirine, delaviridine, efavirenz, etravirine. Other NNRTIs include PNU-142721, a furopyridine-thiopyrimide; capravirine (S-1153 or AG-1 549; 5-(3,5-dichlorophenyl)-thio-4-isopropyl-1-(4-pyridyl)methyl-1H-imidazol-2-ylm-ethyl carbonate); emivirine [MKC-442; (1-(ethoxy-methyl)-5-(1-methyethyl)-6-(phenylmethyl)-(2,4(1H,3H)-pyrimidinedione)]; (+)-calanolide A (NSC-67545 1) and B, coumarin derivatives; DAPY (TMC120; 4-{4-[4-((E)-2-cyano-vinyl)-2,6-dimethyl-phenylamino]-pyrimidin-2-ylamino-}-benzonitrile); BILR-355 BS (12-ethyl-8-[2-(1-hydroxy-quinolin-4-yloxy)-ethyl]-5-methyl-11,12-dihydro-5H-1,5,10,12-tetraaza-dibenzo[a,e]cycloocten-6-one; PHI-236 (7-bromo-3-[2,5-dimethoxy-phenyl)-ethyl]-3,4-dihydro-1H-pyrido[1,2-a][-1,3,5]triazine-2-thione) and PHI-443 (TMC-278, 1-(5-bromo-pyridin-2-yl)-3-(2-thiophen-2-yl-ethyl)-thiourea).

Suitable protease inhibitors (PIs) that may be employed in the pharmaceutical composition of the present invention may comprise saquinavir; ritonavir; nelfinavir; amprenavir; lopinavir, indinavir; nelfinavir; atazanavir; lasinavir; palinavir; tipranavir; fosamprenavir; darunavir; TMC114; DMP450, a cyclic urea; BMS-2322623, BMS-232623; GS3333; KNI-413; KNI-272; LG-71350; CGP-61755; PD 173606; PD 177298; PD 178390; PD 178392; U-140690; ABT-378; and AG-1549 an imidazole carbamate. Additional PIs include N-cycloalkylglycines, α-hydroxyarylbutanamides; α-hydroxy-γ-[[(carbocyclic- or heterocyclic-substituted)amino)carbonyl]alkanamide derivatives; γ-hydroxy-2-(fluoroalkylaminocarbonyl)-1-piperazinepentanamides; dihydropyrone derivatives and α- and β-amino acid hydroxyethylaminosulfonamides; and N-aminoacid substituted L-lysine derivatives.

The antiretroviral agents according to the present invention may be used in the form of salts or esters derived from inorganic or organic acids. These salts include but are not limited to acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkylsulfates like dimethyl, diethyl, dibutyl, and diamylsulfates, long chain halides such as decyl, lauryl, myristyl and stearyl chlorides, bromides and iodides, aralkyl halides like benzyl and phenethyl bromides, and the like.

Preferably, the pharmaceutical composition comprises dolutegravir, tenofovir and emtricitabine/lamivudine optionally with one or more pharmaceutically acceptable excipients.

Alternatively, the pharmaceutical composition comprises elvitegravir, tenofovir and lamivudine optionally with one or more pharmaceutically acceptable excipients.

Alternatively, the pharmaceutical composition comprises elvitegravir, tenofovir and emtricitabine optionally with one or more pharmaceutically acceptable excipients.

Alternatively, the pharmaceutical composition comprises raltegravir, tenofovir and emtricitabine/lamivudine optionally with one or more pharmaceutically acceptable excipients.

Alternatively, the pharmaceutical composition comprises dolutegravir, lamivudine and zidovudine optionally with one or more pharmaceutically acceptable excipients.

Alternatively, the pharmaceutical composition comprises elvitegravir, lamivudine and zidovudine optionally with one or more pharmaceutically acceptable excipients.

Alternatively, the pharmaceutical composition comprises raltegravir, lamivudine and zidovudine optionally with one or more pharmaceutically acceptable excipients.

Alternatively, the pharmaceutical composition comprises dolutegravir, emtricitabine and lamivudine/zidovudine optionally with one or more pharmaceutically acceptable excipients.

Alternatively, the pharmaceutical composition comprises dolutegravir, tenofovir and zidovudine optionally with one or more pharmaceutically acceptable excipients.

Alternatively, the pharmaceutical composition comprises raltegravir, emtricitabine and lamivudine/zidovudine optionally with one or more pharmaceutically acceptable excipients.

Alternatively, the pharmaceutical composition comprises raltegravir, tenofovir and zidovudine optionally with one or more pharmaceutically acceptable excipients.

Alternatively, the pharmaceutical composition comprises dolutegravir, abacavir and lamivudine optionally with one or more pharmaceutically acceptable excipients.

Alternatively, the pharmaceutical composition comprises raltegravir, abacavir and lamivudine optionally with one or more pharmaceutically acceptable excipients.

Alternatively, the pharmaceutical composition comprises dolutegravir, abacavir and emtricitabine optionally with one or more pharmaceutically acceptable excipients.

Alternatively, the pharmaceutical composition comprises raltegravir, abacavir and emtricitabine optionally with one or more pharmaceutically acceptable excipients.

Suitably, the pharmaceutical composition according to the present invention are presented in solid dosage form suitable for oral or buccal administration, however, other dosage forms such as liquid dosage form may be envisaged under the ambit of the invention.

The pharmaceutical composition according to the present invention may be administered orally through unit dosage forms including tablets, capsules (filled with powders, pellets, beads, mini-tablets, pills, micro-pellets, small tablet units, MUPS, disintegrating tablets, dispersible tablets, granules, and microspheres, multiparticulates), sachets (filled with powders, pellets, beads, mini-tablets, pills, micro-pellets, small tablet units, MUPS, disintegrating tablets, dispersible tablets, granules, and microspheres, multiparticulates) and sprinkles, however, other dosage forms such as controlled release formulations, lyophilized formulations, modified release formulations, delayed release formulations, extended release formulations, pulsatile release formulations, dual release formulations and the like; liquid dosage form (liquids, suspensions, solutions, emulsions, microemulsions, sprays, spot-on), injection preparations, nano formulation, self emulsifying drug delivery formulations etc. may also be envisaged under the ambit of the invention.

Suitably, the pharmaceutical antiretroviral composition according to the present invention may also be presented in the form of a kit comprising at least one integrase inhibitor and at least one antiretroviral or anti-HIV agent and provides the patient with his daily regimen of drugs in a single package. This further facilitates the patient in getting the drug regimen of the entire day in a single package which also enables the patient to avoid carrying of numerous medications and also confirm if the same are administered. The kit composition has an advantage over the other packaged dosage forms in that the patient always has access to the set of instructions for administration contained in the kit. The inclusion of a set of instructions for administration has been shown to improve patient compliance.

Preferably, the present invention provides a pharmaceutical antiretroviral composition comprising dolutegravir, tenofovir, emtricitabine/lamivudine and zidovudine in a kit form.

Alternatively, the present invention provides a pharmaceutical antiretroviral composition comprising raltegravir, tenofovir, emtricitabine/lamivudine and zidovudine in a kit form.

Alternatively, the pharmaceutical antiretroviral composition in a kit form may comprise a separate unit dosage form of dolutegravir/raltegravir, a separate unit dosage form of tenofovir, separate unit dosage form of emtricitabine/lamivudine and separate unit dosage form of zidovudine.

The mini-tablets or granules filled in hard gelatin capsules or sachets can be directly administered or can be administered by sprinkling the mini-tablet or granules on regular meals. Alternatively, the mini-tablets or granules filled in hard gelatin capsules or sachets may be administered with liquid or semi-solid beverages such as but not limited to, juices, water.

The mini-tablets or granules according to the present invention may also optionally be coated. Preferably, mini-tablets or granules according to the present invention may be film coated. More preferably, the mini-tablets or granules may be seal coated and then film coated and further filled in hard gelatin capsules or sachets.

A tablet formulation is the preferred solid dosage form due to its greater stability, less risk of chemical interaction between different medicaments, smaller bulk, accurate dosage, and ease of production.

Solid unit dosage forms are preferably in the form of tablets either single or bilayered or multilayered tablets but other conventional dosages such as powders, pellets, capsules and sachets may fall within the scope of this invention.

The pharmaceutical antiretroviral composition may be administered simultaneously, separately or sequentially in a single unit dosage form.

The pharmaceutical antiretroviral composition may be administered as a single layered or bilayered or multilayered tablet wherein each layer may or may not contain drug/drugs along with pharmaceutically acceptable excipients which are then compressed to provide either a single layered, bilayered or multilayered tablet.

Suitable excipients may be used for formulating the various dosage forms.

The term excipient used herein includes one or more of pharmaceutically acceptable ingredients but are not limited to carriers, diluents or fillers, binders, lubricants, glidants and disintegrants.

Non-limiting examples of suitable pharmaceutically acceptable carriers, diluents or fillers for use in the pharmaceutical composition include lactose (for example, spray-dried lactose, $\alpha$-lactose, $\beta$-lactose) lactose available under the trade mark Tablettose, various grades of lactose available under the trade mark Pharmatose or other commercially available forms of lactose, lactitol, saccharose, sorbitol, mannitol, dextrates, dextrins, dextrose, maltodextrin, croscarmellose sodium, microcrystalline cellulose (for example, microcrystalline cellulose available under the trade mark Avicel), hydroxypropylcellulose, L-hydroxypropylcellulose (low substituted), hydroxypropyl methylcellulose (HPMC), methylcellulose polymers (such as, for example, Methocel A, Methocel A4C, Methocel A15C, Methocel A4M), hydroxyethylcellulose, sodium carboxymethylcellulose, carboxymethylene, carboxymethyl hydroxyethylcellulose and other cellulose derivatives, pre-gelatinized starch, starches or modified starches (including potato starch, corn starch, maize starch and rice starch) and the like.

Typically glidants and lubricants may also be included in the pharmaceutical composition. Non-limiting examples include stearic acid and pharmaceutically acceptable salts or esters thereof (for example, magnesium stearate, calcium stearate, sodium stearyl fumarate or other metallic stearate), talc, waxes (for example, microcrystalline waxes) and glycerides, light mineral oil, PEG, silica acid or a derivative or salt thereof (for example, silicates, silicon dioxide, colloidal silicon dioxide and polymers thereof, crospovidone, magnesium aluminosilicate and/or magnesium alumina metasilicate), sucrose ester of fatty acids, hydrogenated vegetable oils (for example, hydrogenated castor oil), or mixtures thereof or any other suitable lubricant.

Suitably one or more binders may also be present in the pharmaceutical composition and non-limiting examples of suitable binders are, for example, polyvinyl pyrrolidone (also known as povidone), polyethylene glycol(s), acacia, alginic acid, agar, calcium carragenan, cellulose derivatives such as ethyl cellulose, methyl cellulose, hydroxypropyl cellulose, hydroxypropyl methyl cellulose, sodium carboxymethylcellulose, dextrin, gelatin, gum arabic, guar gum, tragacanth, sodium alginate, or mixtures thereof or any other suitable binder.

Suitable disintegrants may also be present in the pharmaceutical composition.

Examples include, but are not limited to, hydroxylpropyl cellulose (HPC), low density HPC, carboxymethylcellulose (CMC), sodium CMC, calcium CMC, croscarmellose sodium; starches exemplified under examples of fillers and also carboxymethyl starch, hydroxylpropyl starch, modified starch; crystalline cellulose, sodium starch glycolate; alginic acid or a salt thereof, such as sodium alginate or their equivalents and any combination thereof.

There is also provided a hot melt extruded pharmaceutical composition comprising antiretroviral drug(s), for example at least one integrase inhibitor and at least one antiretroviral agent or anti-HIV agent as described previously, and at least one water soluble and/or water swellable and/or water insoluble polymer or combination thereof and optionally one or more pharmaceutically acceptable excipients.

Water soluble polymers which may be used in the pharmaceutical composition of the present invention, include, but are not limited to, homopolymers and co-polymers of N-vinyl lactams, especially homopolymers and co-polymers of N-vinyl pyrrolidone e.g. polyvinylpyrrolidone (PVP), co-polymers of PVP and vinyl acetate, co-polymers of N-vinyl pyrrolidone and vinyl acetate (Copovidone) or vinyl propionate, dextrins such as grades of maltodextrin, cellulose esters and cellulose ethers, high molecular polyalkylene oxides such as polyethylene oxide and polypropylene oxide and co-polymers of ethylene oxide, propylene oxide and mixtures thereof.

Water insoluble polymers which may be used in the pharmaceutical composition of the present invention, include, but are not limited to, acrylic copolymers e.g. Eudragit E100 or Eudragit EPO; Eudragit L30D-55, Eudragit FS30D, Eudragit RL30D, Eudragit RS30D, Eudragit NE30D, Acryl-Eze; polyvinylacetate, for example, Kollicoat SR 30D; cellulose derivatives such as ethylcellulose, cellulose acetate e.g. Surelease, Aquacoat ECD and Aquacoat CPD and mixtures thereof.

Water swellable polymers that may be used in the pharmaceutical composition of the present invention include but are not limited to polyethylene oxide; poly (hydroxy alkyl methacrylate); poly (vinyl) alcohol, having a low acetal residue, which is cross-linked with glyoxal, formaldehyde or glutaraldehyde and having a degree of polymerization of from 200 to 30,000; a mixture of methyl cellulose, cross-linked agar and carboxymethyl cellulose; Carbopol® carbomer which is an acidic carboxy polymer; Cyanamer® polyacrylamides; cross-linked water swellable indene-maleic anhydride polymers; Goodrich® polyacrylic acid; starch graft copolymers; Aqua Keeps® acrylate polymer polysaccharides composed of condensed glucose units such as diester cross-linked polyglucan, and the like; Amberlite® ion exchange resins; Explotab® sodium starch glycolate; Ac-Di-Sol® croscarmellose sodium or mixtures thereof.

The one or more optional pharmaceutically acceptable excipients may include a plasticizer.

Plasticizers reduce the viscosity of the polymer melt and thereby allow for lower processing temperature and extruder torque during hot melt extrusion. They further decrease the glass transition temperature of the polymer.

Plasticizers which may be used in the pharmaceutical composition of the present invention, include, but are not limited to, polysorbates such as sorbitan monolaurate (Span 20), sorbitan monopalmitate, sorbitan monostearate, sorbitan monoisostearate; citrate ester type plasticizers like triethyl citrate, citrate phthalate; propylene glycol; glycerin; polyethylene glycol (low & high molecular weight); triacetin; dibutylsebacate, tributylsebacate; dibutyltartrate, dibutyl phthalate, glycerol palmitosterate and mixtures thereof.

The pharmaceutical composition may be prepared by admixing at least one integrase inhibitor, at least one antiretroviral or anti HIV agent according to the present invention with other suitable pharmaceutically acceptable excipients such as sweeteners, vehicle/wetting agents, buffering agents, coloring agents, flavoring agents, preservatives, viscosity enhancing/thickening agents and the like or combinations thereof.

The pharmaceutical composition of the present invention may be prepared by admixing the at least one integrase inhibitor, the at least one antiretroviral or anti-HIV agent either separately or in combination, optionally, with one or more pharmaceutically acceptable excipients. This blend may be subjected to granulation or directly compacted to obtain granules.

The pharmaceutical composition according to the present invention may be prepared through various techniques or processes known in the art which includes, but are not limited to direct compression, wet granulation, roll compaction, dry granulation, melt granulation, melt extrusion, spray drying, solution evaporation or combinations thereof.

It may be acknowledged by a person skilled in the art that the above mentioned techniques may either be used alone or in combination thereof.

The pharmaceutical composition of the present invention can be processed by roll compaction.

The process comprises sifting and dry mixing the at least one integrase inhibitor, the at least one antiretroviral agent or anti-HIV agent and optionally with one or more excipients followed by compaction and sizing to obtain granules.

The process further comprises lubricating the granules and either compressing the lubricated granules to form a single layered tablet, bi/multi layered tablet or a mini-tablet; or filling the lubricated granules into hard gelatin capsules or sachets.

The pharmaceutical composition according to the present invention may also optionally be coated, i.e. seal coated or film coated. Preferably, the pharmaceutical composition may be seal coated and then film coated.

The pharmaceutical composition may be film coated with, but not limited to, Ready colour mix systems (such as Opadry™ colour mix systems) and polyvinyl alcohol-polyethylene glycol copolymer and polyvinyl alcohol.

The pharmaceutical antiretroviral composition may be seal coated followed by film coating using polymeric materials, such as but not limited to hydroxypropylmethylcellulose (HPMC 6 CPS, or HPMC 6 CPS to HPMC 15CPS grade), hydroxypropylcellulose, polyvinylpyrrolidone, methylcellulose, carboxymethylcellulose, hypromellose, acacia, gelatin, and polyvinyl alcohol-polyethylene glycol copolymer and polyvinyl alcohol and the like or combinations thereof.

The pharmaceutical composition of the present invention may be formulated for paediatric patients and from the point of view of paediatric patient acceptability suitable bulking agents may be incorporated, in the pharmaceutical antiretroviral composition comprising saccharides, including monosaccharides, disaccharides, polysaccharides and sugar alcohols but not limited to arabinose, lactose, dextrose, sucrose, fructose, maltose, mannitol, erythritol, sorbitol, xylitol, lactitol, powdered cellulose, microcrystalline cellulose, purified sugar and their derivatives and the like or combinations thereof.

Accordingly, the pharmaceutical composition of the present invention may further incorporate suitable pharmaceutically acceptable flavourants, such as, but not limited to, citric acid, tartaric acid, lactic acid, orange permaseal, strawberry cream flavour or other natural flavourants and sweeteners such as, but not limited to, aspartame and the like or combinations thereof.

The pharmaceutical composition according to the present invention may further incorporate suitable pharmaceutically acceptable colourants, such as, but not limited to, red oxide of iron and ferric oxide yellow.

The pharmaceutical composition according to the present invention may also comprise the actives in nano size form. In other words, the at least one integrase inhibitor and/or at least one antiretroviral agent or anti-HIV agent can be in the form of nano-size particles. Preferably, these active pharmaceutical ingredients have average particle size less than about 2000 nm, preferably less than about 1000 nm.

Nanonization of hydrophobic or poorly water-soluble drugs generally involves the production of drug nanocrystals through either chemical precipitation (bottom-up technology) or disintegration (top-down technology). Different methods may be utilized to reduce the particle size of the hydrophobic or poorly water soluble drugs. [Huabing Chen et al., discusses the various methods to develop nano-formulations in "Nanonization strategies for poorly water-soluble drugs," Drug Discovery Today, Volume 00, Number 00, March 2010].

Nano-sizing leads to an increase in the exposure of surface area of particles leading to an increase in the rate of dissolution.

The nanoparticles of the present invention may be obtained by any of the process such as, but not limited to, milling, precipitation, high pressure homogenization, spray freeze drying, super-critical fluid technology, double emulsion or solvent evaporation, Particle replication in non-wetting templates, thermal condensation, ultrasonication and spray drying.

The nano-milled drugs may be obtained by nano-milling of drugs with at least one surface stabilizer, at least one viscosity building agent and at least one polymer.

The present invention provides a method of prevention, treatment or prophylaxis of diseases caused by retroviruses, especially acquired immune deficiency syndrome or an HIV infection, which method comprises administering the pharmaceutical antiretroviral composition substantially as hereinbefore described. There is further provided by the present invention an antiretroviral composition substantially as hereinbefore described, for use in treating disorders or conditions that respond to, or are prevented, ameliorated or eliminated by administering the pharmaceutical antiretroviral composition comprising substantially as hereinbefore described.

The present invention also provides a pharmaceutical composition as substantially described herein by reference to the examples.

The following examples are for the purpose of illustration of the invention only and are not intended in any way to limit the scope of the present invention.

Example 1

Manufacturing Formula

| Part I : Dolutegravir Layer | | |
| --- | --- | --- |
| Sr. No. | Ingredients | Qty (mg)/Tablet |
| Dry Mix | | |
| 1 | Dolutegravir | 50.00 |
| 2 | Microcrystalline Cellulose PH 102 | 415.00 |
| 3 | Croscarmellose Sodium | 25.00 |
| 4 | Colloidal Silicon Dioxide | 2.50 |

| | Blending & Lubrication | |
|---|---|---|
| 5 | Colloidal Silicon Dioxide | 2.50 |
| 6 | Magnesium Stearate | 5.00 |
| | Total weight Part I | 500.00 |

Part II : Tenofovir & Emtricitabine Layer

| Sr. No. | Ingredients | Qty (mg)/Tablet |
|---|---|---|
| | Dry Mix | |
| 1 | Emtricitabine | 200.00 |
| 2 | Tenofovir Disoproxil Fumarate | 300.00 |
| 3 | Microcrystalline Cellulose PH 102 | 50.30 |
| 4 | Croscarmellose Sodium | 31.70 |
| 5 | Red Oxide Of Iron | 0.20 |
| 6 | Magnesium Stearate | 7.70 |
| | Blending & Lubrication | |
| 7 | Croscarmellose Sodium | 16.30 |
| 8 | Magnesium Stearate | 6.80 |
| | Total Weight Part II | 613.00 |
| | Tablet weight (Part I + Part II) | 1113.00 |
| | Film Coating to Bilayer Tablet | |
| 1 | Opadry ™ | 27.00 |
| 2 | Purified Water | q.s. |
| | Final Coated Tablet weight | 1140.00 |

Manufacturing Process:
1. All the materials of each part were sifted & dry mixed in separately.
2. The sifted material was compacted and sized to get the free flowing granules of each part.
3. The granules of each part obtained in step 2 were blended with croscarmellose sodium and lubricated with pre-sifted with Magnesium stearate and then compressed into bilayer tablet.
4. The bilayer tablets were film coated using dispersion of Opadry™.

Example 2

Manufacturing Formula:

| | Part I : Dolutegravir Layer | |
|---|---|---|
| Sr. No. | Ingredients | Qty (mg)/Tablet |
| | Dry Mix | |
| 1 | Dolutegravir | 50.00 |
| 2 | Microcrystalline Cellulose PH 102 | 415.00 |
| 3 | Croscarmellose Sodium | 25.00 |
| 4 | Colloidal Silicon Dioxide | 2.50 |
| | Blending & Lubrication | |
| 5 | Colloidal Silicon Dioxide | 2.50 |
| 6 | Magnesium Stearate | 5.00 |
| | Total weight Part I | 500.00 |

| | Part II : Tenofovir & Lamivudine Layer | |
|---|---|---|
| Sr. No. | Ingredients | Qty (mg)/Tablet |
| I | Tenofovir DF Part | |
| 1 | Tenofovir Disoproxil Fumarate | 300.00 |
| 2 | Croscarmellose Sodium | 22.50 |
| 3 | Microcrystalline Cellulose PH 101 | 45.00 |
| 4 | Ferric Oxide Yellow | 0.20 |
| 5 | Magnesium Stearate | 2.50 |
| II | Lamivudine Part | |
| 6 | Lamivudine | 300.00 |
| 7 | Croscarmellose Sodium | 22.50 |
| 8 | Microcrystalline Cellulose PH 101 | 50.60 |
| 9 | Ferric Oxide Yellow | 0.20 |
| 10 | Pregelatinized Starch | 18.00 |
| 11 | Magnesium Stearate | 2.50 |
| III | Blending & Lubrication | |
| 12 | Croscarmellose Sodium | 30.00 |
| 13 | Magnesium Stearate | 6.00 |
| | Total Weight of Part II | 800.00 |
| | Tablet weight (Part I + Part II) | 1300.00 |
| | Film Coating to Bilayer Tablet | |
| 1 | Opadry ™ | 32.00 |
| 2 | Purified Water | q.s. |
| | Final Coated Tablet weight | 1332.00 |

Manufacturing Process:
1. All the materials of each part were sifted & dry mixed separately.
2. The sifted material was compacted and sized to get the free flowing granules of each part.
3. The granules of each part obtained in step 2 were blended with croscarmellose sodium and lubricated with pre-sifted with Magnesium stearate and then compressed into bilayer tablet.
4. The bilayer tablets were film coated using dispersion of Opadry™.

Example 3

Manufacturing Formula:

| | Part I : Dolutegravir Layer | |
|---|---|---|
| Sr. No. | Ingredients | Qty (mg)/Tablet |
| | Dry Mix | |
| 1 | Dolutegravir | 50.00 |
| 2 | Microcrystalline Cellulose PH 102 | 415.00 |
| 3 | Croscarmellose Sodium | 25.00 |
| 4 | Colloidal Silicon Dioxide | 2.50 |
| | Blending & Lubrication | |
| 5 | Colloidal Silicon Dioxide | 2.50 |
| 6 | Magnesium Stearate | 5.00 |
| | Total weight Part I | 500.00 |

| | Part II : Lamivudine & Zidovudine Layer | |
|---|---|---|
| Sr. No. | Ingredients | Qty (mg)/Tablet |
| 1 | Lamivudine | 150.00 |
| 2 | Zidovudine | 300.00 |
| 3 | Microcrystalline Cellulose PH 102 | 269.42 |

-continued

| | | |
|---|---|---|
| 4 | Colloidal Silicon Dioxide | 2.25 |
| 5 | Sodium Starch Glycolate | 22.50 |
| 6 | Ferric Oxide Yellow | 0.20 |
| | Lubrication | |
| 7 | Magnesium Stearate | 5.63 |
| | Total Weight of Part II | 750.00 |
| | Tablet weight (Part I + Part II) | 1250.00 |
| | Film Coating to Bilayer Tablet | |
| 1 | Opadry ™ | 32.00 |
| 2 | Purified Water | q.s. |
| | Final Coated Tablet weight | 1282.00 |

Manufacturing Process:
1. All the materials of each part were sifted & dry mixed separately.
2. The sifted material was compacted and sized to get the free flowing granules of each part.
3. The granules of each part obtained in step 2 were blended with croscarmellose sodium and lubricated with pre-sifted with Magnesium stearate and then compressed into bilayer tablet.
4. The bilayer tablets were film coated using dispersion of Opadry™.

Example 4

Manufacturing Formula:

| Part I : Raltegravir Layer | | |
|---|---|---|
| Sr. No. | Ingredients | Qty/Tablet |
| 1 | Raltegravir Potassium | 434.40 |
| 2 | MCC PH102 | 114.11 |
| 3 | Lactose Monohydrate | 26.06 |
| 4 | Calcium Phosphate Dibasic Anhydrous | 73.85 |
| 5 | Hypromellose 2208 | 26.06 |
| 6 | Poloxamer 407 (Contains 0.01% BHT) | 173.80 |
| 7 | Sodium Stearyl Fumarate | 8.69 |
| 8 | Magnesium Stearate | 13.03 |
| | Total weight Part I | 870.00 |

| Part II : Tenofovir & Emtricitabine Layer | | |
|---|---|---|
| Sr. No. | Ingredients | Qty/Tablet |
| | Dry Mix | |
| 1 | Emtricitabine | 200.00 |
| 2 | Tenofovir Disoproxil Fumarate | 300.00 |
| 3 | Microcrystalline Cellulose PH 102 | 50.30 |
| 4 | Croscarmellose Sodium | 31.70 |
| 5 | Red Oxide Of Iron | 0.20 |
| 6 | Magnesium Stearate | 7.70 |
| | Blending & Lubrication | |
| 7 | Croscarmellose Sodium | 16.30 |
| 8 | Magnesium Stearate | 6.80 |
| | Total Weight Part II | 613.00 |
| | Tablet weight (Part I + Part II) | 1483.00 |
| | Film Coating to Bilayer Tablet | |
| 1 | Opadry ™ | 37.00 |
| 2 | Purified Water | q.s. |
| | Final Coated Tablet weight | 1520.00 |

Manufacturing Process:
1. All the materials of each part were sifted & dry mixed separately.
2. The sifted material was compacted and sized to get the free flowing granules of each part.
3. The granules of each part obtained in step 2 were blended with croscarmellose sodium and lubricated with pre-sifted with Magnesium stearate and then compressed into bilayer tablet.
4. The bilayer tablets were film coated using dispersion of Opadry™.

Example 5

Manufacturing Formula:

| Part I : Raltegravir Layer | | |
|---|---|---|
| Sr. No. | Ingredients | Qty/Tablet |
| 1 | Raltegravir Potassium | 434.40 |
| 2 | MCC PH102 | 114.11 |
| 3 | Lactose Monohydrate | 26.06 |
| 4 | Calcium Phosphate Dibasic Anhydrous | 73.85 |
| 5 | Hypromellose 2208 | 26.06 |
| 6 | Poloxamer 407 (Contains 0.01% BHT) | 173.80 |
| 7 | Sodium Stearyl Fumarate | 8.69 |
| 8 | Magnesium Stearate | 13.03 |
| | Total weight of part I | 870.00 |

| Part II : Tenofovir & Lamivudine Layer | | |
|---|---|---|
| Sr. No. | Ingredients | Qty/Tablet |
| I | Tenofovir DF Part | |
| 1 | Tenofovir Disoproxil Fumarate | 300.00 |
| 2 | Croscarmellose Sodium | 22.50 |
| 3 | Microcrystalline Cellulose PH 101 | 45.00 |
| 4 | Ferric Oxide Yellow | 0.20 |
| 5 | Magnesium Stearate | 2.50 |
| II | Lamivudine Part | |
| 6 | Lamivudine | 300.00 |
| 7 | Croscarmellose Sodium | 22.50 |
| 8 | Microcrystalline Cellulose PH 101 | 50.60 |
| 9 | Ferric Oxide Yellow | 0.20 |
| 10 | Pregelatinized Starch | 18.00 |
| 11 | Magnesium Stearate | 2.50 |
| III | Blending & Lubrication | |
| 12 | Croscarmellose Sodium | 30.00 |
| 13 | Magnesium Stearate | 6.00 |
| | Total Weight of Part II | 800.00 |
| | Tablet weight (Part I + Part II) | 1670.00 |
| | Film Coating to Bilayer Tablet | |
| 1 | Opadry ™ | 42.00 |
| 2 | Purified Water | q.s. |
| | Final Coated Tablet weight | 1712.00 |

Manufacturing Process:
1. All the materials of each part were sifted & dry mixed separately.
2. The sifted material was compacted and sized to get the free flowing granules of each part.
3. The granules of each part obtained in step 2 were blended with croscarmellose sodium and lubricated with pre-sifted with Magnesium stearate and then compressed into bilayer tablet.

4. The bilayer tablets were film coated using dispersion of Opadry™.

Example 6

Manufacturing Formula:

| Part I : Raltegravir Layer | | |
|---|---|---|
| Sr. No. | Ingredients | Qty/Tablet |
| 1 | Raltegravir Potassium | 434.40 |
| 2 | MCC PH102 | 114.11 |
| 3 | Lactose Monohydrate | 26.06 |
| 4 | Calcium Phosphate Dibasic Anhydrous | 73.85 |
| 5 | Hypromellose 2208 | 26.06 |
| 6 | Poloxamer 407 (Contains 0.01% BHT) | 173.80 |
| 7 | Sodium Stearyl Fumarate | 8.69 |
| 8 | Magnesium Stearate | 13.03 |
| | Total weight of part I | 870.00 |

| Part II : Lamivudine & Zidovudine Layer | | |
|---|---|---|
| Sr. No. | Ingredients | Qty/Tablet |
| 1 | Lamivudine | 150.00 |
| 2 | Zidovudine | 300.00 |
| 3 | Microcrystalline Cellulose PH 102 | 269.42 |
| 4 | Colloidal Silicon Dioxide | 2.25 |
| 5 | Sodium Starch Glycolate | 22.50 |
| 6 | Ferric Oxide Yellow | 0.20 |
| | Lubrication | |
| 7 | Magnesium Stearate | 5.63 |
| | Total Weight of Part II | 750.00 |
| | Tablet weight (Part I + Part II) | 1620.00 |
| | Film Coating to Bilayer Tablet | |
| 1 | Opadry ™ | 40.00 |
| 2 | Purified Water | q.s. |
| | Final Coated Tablet weight | 1660.00 |

Manufacturing Process:
1. All the materials of each part were sifted & dry mixed separately.
2. The sifted material was compacted and sized to get the free flowing granules of each part.
3. The granules of each part obtained in step 2 were pre-sifted with Magnesium stearate and then compressed into bilayer tablet.
4. The bilayer tablets were film coated using dispersion of Opadry™.

Example 7

Manufacturing Formula:

| Sr. No. | Ingredients | Qty (mg)/Tablet |
|---|---|---|
| | Dry Mix | |
| 1 | Dolutegravir | 50.00 |
| 2 | Emtricitabine | 200.00 |
| 3 | Tenofovir Disoproxil Fumarate | 300.00 |
| 4 | Microcrystalline Cellulose PH 102 | 350.00 |
| 5 | Croscarmellose Sodium | 25.00 |
| | Binder | |
| 6 | Hypromellose E15 cps | 20.00 |
| 7 | Purified Water | q.s. |
| | Blending & Lubrication | |
| 8 | Colloidal Silicon Dioxide | 2.50 |
| 9 | Microcrystalline Cellulose PH 102 | 50.00 |
| 10 | Croscarmellose Sodium | 25.00 |
| 11 | Magnesium Stearate | 7.50 |
| | Total weight uncoated tablet | 1030.00 |
| | Film Coating | |
| 12 | Opadry ™ | 25.00 |
| 13 | Purified Water | q.s. |
| | Final Coated Tablet weight | 1055.00 |

Manufacturing Process:
1. All the materials of each part were sifted & dry mixed separately.
2. Binder solution was prepared by adding hypromellose in purified water
3. The granules were prepared by spraying binder solution of step 2 on to the dry mix.
4. The granules obtained were sized and blended with colloidal silicon dioxide, microcrystalline cellulose and croscarmellose sodium and further lubricated with magnesium stearate.
5. The lubricated granules of step 4 were compressed to form tablets and then film coated with Opadry™ dispersion.

Example 8

Manufacturing Formula:

| Sr. No. | Ingredients | Qty (mg)/Tablet |
|---|---|---|
| | Dry Mix | |
| 1 | Dolutegravir | 50.00 |
| 2 | Tenofovir Disoproxil Fumarate | 300.00 |
| 3 | Lamivudine | 300.00 |
| 4 | Microcrystalline Cellulose PH 102 | 395.50 |
| 5 | Croscarmellose Sodium | 25.00 |
| | Binder | |
| 6 | Hypromellose E15 cps | 23.00 |
| 7 | Purified Water | q.s. |
| | Blending & Lubrication | |
| 8 | Colloidal Silicon Dioxide | 2.50 |
| 9 | Microcrystalline Cellulose PH 102 | 50.00 |
| 10 | Magnesium Stearate | 9.00 |
| | Total weight Uncoated tablet | 1155.00 |
| | Film Coating | |
| 11 | Opadry ™ | 25.00 |
| 12 | Purified Water | q.s. |
| | Final Coated Tablet weight | 1180.00 |

Manufacturing Process:
1. All the materials of each part were sifted & dry mixed separately.
2. Binder solution was prepared by adding hypromellose in purified water 3. The granules were prepared by spraying binder solution of step 2 on to the dry mix.
4. The granules obtained were sized and blended with colloidal silicon dioxide, microcrystalline cellulose and further lubricated with magnesium stearate.
5. The lubricated granules of step 4 were compressed to form tablets and then film coated with Opadry™ dispersion.

Example 9

Manufacturing Formula:

| Sr. No. | Ingredients | Qty (mg)/Tablet |
|---|---|---|
| | Dry Mix | |
| 1 | Dolutegravir | 50.00 |
| 2 | Lamivudine | 150.00 |
| 3 | Zidovudine | 300.00 |
| 4 | Microcrystalline Cellulose PH 102 | 395.00 |
| 5 | Croscarmellose Sodium | 25.00 |
| | Binder | |
| 6 | Hypromellose E15 cps | 20.00 |
| 7 | Purified Water | q.s. |
| | Blending & Lubrication | |
| 8 | Colloidal Silicon Dioxide | 2.50 |
| 9 | Microcrystalline Cellulose PH 102 | 50.00 |
| 10 | Magnesium Stearate | 7.50 |
| | Total weight uncoated tablet | 1000.00 |
| | Film Coating | |
| 1 | Opadry ™ | 25.00 |
| 2 | Purified Water | q.s. |
| | Final Coated Tablet weight | 1025.00 |

Manufacturing Process:
1. All the materials of each part were sifted & dry mixed separately.
2. Binder solution was prepared by adding hypromellose in purified water
3. The granules were prepared by spraying binder solution of step 2 on to the dry mix.
4. The granules obtained were sized and blended with colloidal silicon dioxide, microcrystalline cellulose and further lubricated with magnesium stearate.
5. The lubricated granules of step 4 were compressed to form tablets and then film coated with Opadry™ dispersion.

It will be readily apparent to one skilled in the art that varying substitutions and modifications may be made to the invention disclosed herein without departing from the spirit of the invention. Thus, it should be understood that although the present invention has been specifically disclosed by the preferred embodiments and optional features, modification and variation of the concepts herein disclosed may be resorted to by those skilled in the art, and such modifications and variations are considered to be falling within the scope of the invention.

It is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It must be noted that, as used in this specification and the appended claims, the singular forms "a," "an" and "the" include plural references unless the context clearly dictates otherwise. Thus, for example, reference to "a polymer" includes a single polymer as well as two or more different polymers; reference to a "plasticizer" refers to a single plasticizer or to combinations of two or more plasticizer, and the like.

What is claimed is:

1. A pharmaceutical composition that is a single unit dosage form for oral administration in the form of a coated bi-layer tablet comprising a first layer and a second layer,
    wherein the first layer comprises from about 1 mg to about 50 mg dolutegravir or its pharmaceutically acceptable salt thereof, and one or more pharmaceutically acceptable excipients; and
    wherein the second layer comprises from about 150 mg to about 300 mg of tenofovir disoproxil fumarate, from about 150 mg to about 300 mg of lamivudine, and pharmaceutically acceptable excipients.

2. The pharmaceutical composition according to claim 1, wherein tenofovir disoproxil fumarate is present in an amount of 300 mg.

3. The pharmaceutical composition according to claim 1, wherein lamivudine is present in an amount of 300 mg.

4. The pharmaceutical composition according to claim 1, wherein the composition further comprises one or more pharmaceutically acceptable excipients selected from carriers, diluents, fillers, binders, lubricants, glidants, disintegrants, bulking agents, flavourants or any combination thereof.

5. The pharmaceutical composition according to claim 1, wherein the composition is in the form of a tablet, minitablet, granules, sprinkles, capsules, sachets, powders, pellets, a liquid dosage form, injection preparation or in the form of a kit.

6. The pharmaceutical composition according to claim 1, for use in the treatment of diseases caused by retroviruses.

7. A process for preparing the pharmaceutical composition as claimed in claim 1, wherein the process comprises the steps of:
    forming a first layer by admixing dolutegravir with one or more pharmaceutically acceptable excipients;
    forming a second layer by admixing tenofovir disoproxil fumarate, lamivudine, and pharmaceutically acceptable excipients; and
    after forming the first layer and the second layer, combining the first layer and the second layer to form a bi-layer tablet.

8. The process according to claim 7, comprising the steps of: (a) sifting and dry mixing the dolutegravir and pharmaceutically acceptable excipients, and (b) forming granules of the dolutegravir and optionally pharmaceutically acceptable excipients.

9. A process comprising utilizing the pharmaceutical composition according to claim 1, in the manufacture of a medicament for the treatment of diseases caused by retroviruses.

10. A method of treating diseases caused by retroviruses wherein the method comprises administering the pharmaceutical composition according to claim 1 to a subject in need thereof.

11. The method according to claim 10, wherein the treatment for diseases caused by retroviruses includes the treatment of acquired immune deficiency syndrome or an HIV infection.

* * * * *